US00PP11428P

United States Patent [19]

Shinozaki et al.

[11] Patent Number: Plant 11,428

[45] Date of Patent: Jun. 27, 2000

[54] GLYCERIA PLANT NAMED 'GLY-P'

[75] Inventors: Satoshi Shinozaki; Hiroyuki Sano; Naoya Hiruma; Takahiro Imada; Munehiro Noda; Fumiyoshi Akaike; Sachiko Yamashima; Madoka Kon, all of Shizuoka, Japan

[73] Assignee: Shibaura Institute of Technology, Tokyo, Japan

[21] Appl. No.: 08/938,751

[22] Filed: Sep. 26, 1997

[51] Int. Cl.[7] ..... A01H 1/00

[52] U.S. Cl. ..... Plt./388

[58] Field of Search ..... Plt./90, 384, 388

[56] References Cited

U.S. PATENT DOCUMENTS

P.P. 8,788 6/1994 Marousky et al. ..... Plt./90

P.P. 9,395 12/1995 Krkland et al. ..... Plt./90.1

P.P. 9,847 4/1997 Riordan et al. ..... Plt./90

OTHER PUBLICATIONS

Taper, et al., "Detection and Measurement of the Alkaloid Peramine in Endophyte–infected Grasses", Journal of Chromatography, 463, (1989) pp. 131–138.

*Primary Examiner*—Howard J. Locker
*Assistant Examiner*—Ashwin D. Mehta
*Attorney, Agent, or Firm*—Armstrong, Westerman, Hattori, McLeland & Naughton

[57] ABSTRACT

The present invention relates to a variety obtained by selecting and cross-breeding those individuals producing the insect resistance substance peramine from *Glyceria ischyroneura* Steud. growing wild in various districts of Japan.

1 Drawing Sheet

BACKGROUND OF THE INVENTION

The present invention provides, as a novel lawn grass, 'Gly-P' which is a select individual of the gramineous plant *Glyceria ischyroneura* Steud.

As conventional lawn grasses, cold district type grasses such as *Zoysia japonica*, Korean lawn grass, Bermuda grass and St. Augustine grass and warm district type grasses such as bent grass, fescue, bluegrass and ryegrass may be enumerated. These lawn grasses are widely used in parks, golf courses, competition grounds such as soccer grounds and racecourses, and many other places. Since a single variety of these lawn grasses is planted on a broad area, a great deal of damage will be done once there is an outbreak of a pest against the variety. It is the present situation that pest control is performed by application of agricultural chemicals and by means of a pheromone trap and the like.

Recently, partly due to the influence from the warming of the earth and environmental dirsuption, damage from unusual occurrence of pests is increasing. Under such circumstances, the amount of agricultural chemical application is increasing year by year and its influence upon the environment is of concern.

In order to solve such agricultural chemical problems, introduction of an insect resistance gene into a plant using biotechnology has been tried. However, in order to create a desired plant, a technology of high level and sufficient facilities are needed. Thus, generally, it is difficult to apply this technology to plants.

As a lawn grass producing an insect resistance substance, tall fescue (one of the fescues), a perennial ryegrass (one of the ryegrasses) and the like are known. It is known that an endophyte (a symbiotic microorganism) is associated with the insect resistance substance of these lawn grasses. Thus, among those gramineous plants used as a lawn grass, individuals producing the insect resistance substance peramine are limited.

It is an object of the invention to provide a lawn grass which is able to reduce the amount of agricultural chemical application needed for pest control by means of the insect resistance substance peramine produced by 'Gly-P' itself.

SUMMARY OF THE INVENTION

Toward the solution of the above-mentioned object, the inventors of the present invention have collected and transplanted the wild-type gramineous plant *Glyceria ischyroneura* Steud. growing throughout Japan. From the ecotypes collected, those individuals which produce the insect resistance substance peramine were selected and transplanted. 'Gly-P' was selected from cross-breeding of the open type in the applicants' field of the selected plants. Then, an insect resistance assay was performed on 'Gly-P' using larvae of *Pediasia teterrellus* Zincken, a major pest against lawn grasses. Thus, the present invention has been achieved.

The gramineous plant *Glyceria ischyroneura* Steud. used in the invention grows in watery or marshy districts such as paddy fields, ponds, swamps, mountain streams, etc., and was once a strong weed in paddy fields [Takemasa Nagata, Illustrated Japanese Gramineous Plants (revised and enlarged edition)].

The select individual 'Gly-P' has in its plant body an acremonium type or neotyphodium type endophyte living together and contains peramine. This peramine is known to be an insect resistance substance. Among those gramineous plants used as lawn grasses, tall fescue and perennial ryegrass are known to produce peramine and these plants have been reported to have repellent effect upon *Pediasia teterrellus* Zincken, grain aphid and a certain species of Rhynchophoridae insects [Hironori Koga, Study of Lawn Grass, vol. 22, No. 2, pp. 60–69 (1993)]. These lawn grasses are planted widely in golf courses, etc., since the use of them can reduce the amount of agricultural chemicals applied.

Although *Glyceria ischyroneura* Steud. naturally grows in a wet land, its growth does not decline under dry conditions when this grass is planted in a field and controlled as a lawn grass. Further, because of its vigorous tillering and the development of upright stems from each node which are morphological characteristics of *Glyceria ischyroneura*

Steud., a close turf can be formed by performing usual lawn grass management.

The peramine producing 'Gly-P' is not significantly morphologically different from non-peramine producing strains. By applying the morphological characteristics of *Glyceria ischyroneura* Steud. and the utility of 'Gly-P' as a lawn grass, it is possible to use 'Gly-P' as a lawn grass which can be managed with less agricultural chemicals.

According to the present invention, it is possible to greatly reduce the damage from *Pediasia teterrellus* Zincken, a major pest against lawn grasses, by using as a lawn grass 'Gly-P' selected from *Glyceria ischyroneura* Steud. As a result, *Glyceria ischyroneura* Steud. variety 'Gly-P' of the invention can reduce the amount of agricultural chemical application.

DESCRIPTION OF THE NEW VARIETY

Figure 1:
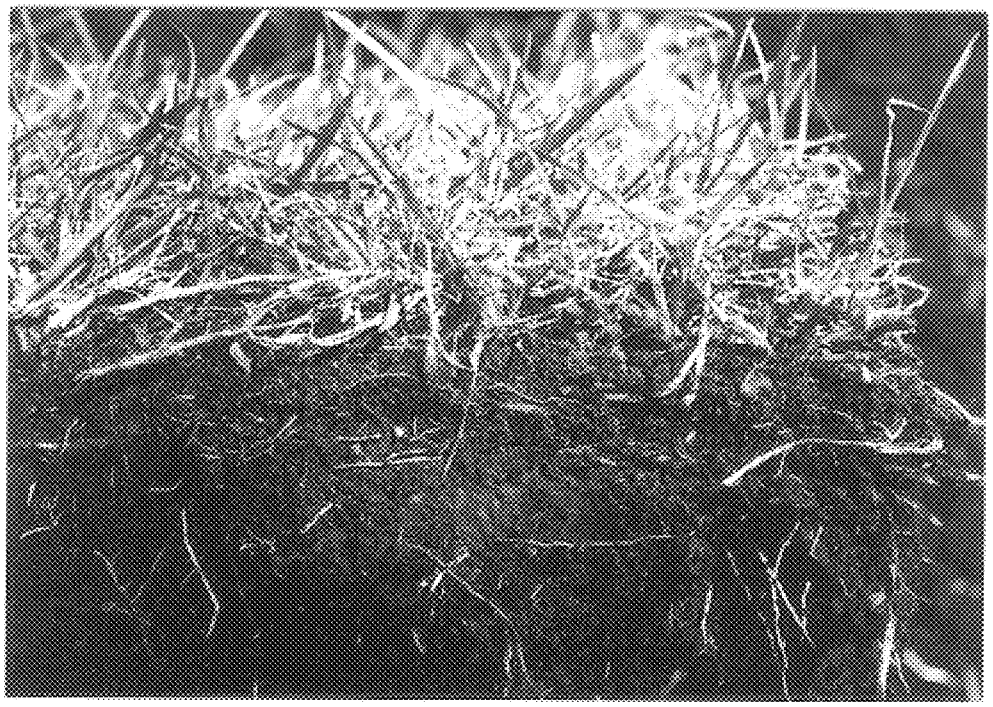
FIG. 1 is a photograph of 'Gly-P' (an enlarged photograph)
Figure 2:
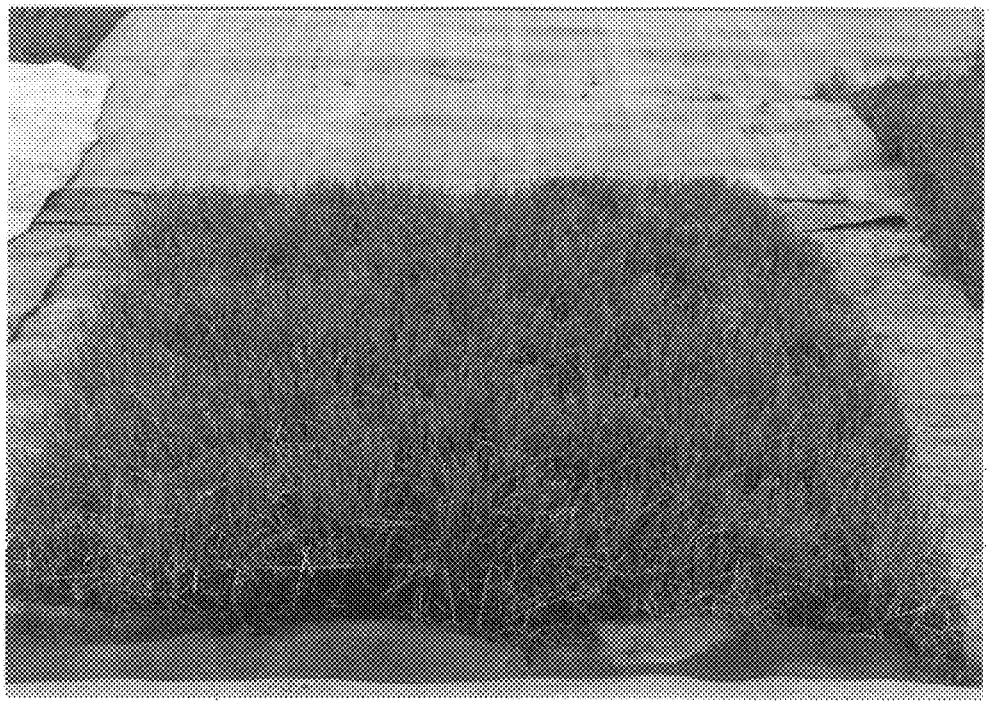
FIG. 2 is a photograph of 'Gly-P'.

The following is a detailed description of the new peramine-containing variety. Wherein dimensions are given, it is to be understood that such characteristics are approximations of averages set forth as accurately as practicable.

Mature plant height: 50–120 cm.

Blade shape: Flat, long.

Rate of growth: Slow, same as for the "Super Short Stop" tall fescue variety.

Growth habit: The germination rate can be increased by peeling the seed coat. Almost all seeds germinate about two weeks after sowing under conditions of continuous light and 25° C. When the seeds are sown in the spring, the flowers do not bloom within the year, but bloom the following year. The flowering season is from May to July. The seeds can be collected from the last eleven days in May. The time of seed collection is about one month earlier than for tall fescue. 'Gly-P' is a perennial plant.

Panicle length: 120–280 mm.

Spikelet length: 4–7 mm.

Spikelet width: 1.5–2.5 mm.

Seed weight: 1,000 seeds weigh about 0.48 g.

Seed yield: About 170 seeds can be collected from an inflorescence.

Inforescence:

*Inflorescence length.*—17.4±1.8 cm.

*Raceme length.*—8.9±0.2 mm.

*Raceme number.*—47.6±5.8.

Leaf color: Moderate olive green (ISCC-NBS Centroid Color Chart), 146A (The Royal Horticultural Society Colour Chart). No pubescence.

Physical appearance of cultivation: Leaf withering becomes conspicuous from the last ten days of November. 'Gly-P' enters a dormant stage in December. Green leaves become conspicuous from the last ten days in March, and physical appearance of full growth is regained in the middle ten days of April.

Soil adaptation: 'Gly-P' prefers wet clay loam and has adaptability to a wide pH range.

Texture of leaf: Softer than common tall fescue, as soft as common Kentucky Bluegrass.

Root system: Thick roots with deep spread.

Tolerance and resistance: The drought, cold and frost tolerances of 'Gly-P' are the same as those of the common variety of Kentucky Bluegrass. With regard to the disease tolerance, 'Gly-P' has a characteristic of not being subject to rust. 'Gly-P' has a high resistance to Bluegrass webworm (*Pediasia teterrellus* Zincken), Lawn cutworm to (*Spodoptera depravata* Butler) and Black cutworm (*Agrotis ipsilon* Hufnagel). 'Gly-P' has high shade tolerance, which is the same as that of common fine fescue.

(1) Method for Selecting Peramine Producing Strains

Analysis by Thin Layer Chromatography

The detection of peramine by thin layer chromatography and liquid chromatography was performed according to the method of B. A. Tapper, D. D. Rowan and G. C. M. Latch (Journal of Chromatography, 463:133–138 (1989)).

Seventy-three individuals of *Glyceria ischyroneura* Steud. collected from various districts of Japan were planted in pots and managed in a greenhouse. Foliage of each individual was sampled and freeze-dried. 100 mg of the freeze-dried sample was placed in a mortar and crushed. Then, 1.5 ml each of methanol and chloroform were added thereto, mixed, and transferred into a centrifuge tube. The contents were mixed slowly at 18° C. for 30 min, and 3 ml each of n-hexane and water were added thereto and agitated for 30 min. After centrifuging at 2000 rpm for 10 min, an organic layer and an aqueous layer were obtained separately.

With respect to the aqueous layer obtained, 3 ml was purified with a BioRad AG2×8 column and an Analytichem Bond Elut CBA column.

After concentration, 100 μl of 80% methanol was added to the sample.

Then, 100 μl of each sample was applied to a thin plate coated with Merck Silica Gel 60 and another 20 μl of each sample was applied thereto dropwise. After development using a mixture of chloroform, methanol, acetic acid and water (20:10:1:1) as a developer, the sample was analyzed by the TLC (thin layer chromatography) method.

With respect to the organic layer, 200 μl of this sample was placed in a 1 ml Eppendorf tube and the solvent was evaporated completely in a centrifugal evaporator. Then, 200 μl of chloroform was added to solve the pellet. Thereafter, 150 μl of 2% tartaric acid was added and mixed for 10 to 15 min. The resultant mixture was centrifuged at 10000 rpm for 3 min and then the pH was adjusted to 9–10 with 4M NaOH. To this mixture, 200 μl chloroform was added and mixed for 10 to 15 min. Thereafter, the mixture was centrifuged at 1000 rpm for 3 min.

The chloroform layer was obtained and concentrated. To a thin plate coated with Merck Silica Gel 60, 20 μl of each sample was applied. After development using a mixture of chloroform and methanol (9:1) as a developer, the sample was analyzed by the TLC method.

The extracts from the aqueous layer and the organic layer were confirmed with UV after development. Then, color reactions were observed using Ehrlich reagent (1.0 g of p-dimethylbenzaldehyde dissolved in 96% ethanol) and nitrosonaphthol reagent, and Rf values were measured.

As a result, the 'Gly-P' extract in the aqueous layer was confirmed to form a bluish purple spot when Ehrlich reagent was used. From the color reaction with the reagent and the Rf value obtained, this extract was confirmed to be an indole alkaloid.

On the other hand, the 'Gly-P' extract in the organic layer was confirmed to form a bluish purple spot when Ehrlich reagent was used and to form a reddish purple spot when nitrosonaphthol reagent was used. From the color reactions with the reagents and the Rf value obtained, this extract was confirmed to be an indole alkaloid.

However, with respect to strains other than 'Gly-P', no color reaction was observed for both the aqueous layer and the organic layer when Ehrlich reagent and Dragendorff reagent were used. Thus, those indole alkaloids are only produced by 'Gly-P'.

(2) Method for Selecting Peramine Producing Strains

Analysis by Liguid Chromatography

An aliquot of the aqeuous layer to which the sample was extracted was passed through a monolayer Analytichem Bond Elut CBA column packed with 100 mg of ion exchange resin regenerated into ammonia form to adsorb peramine.

The column was washed with 1 ml of water. After the washing, peramine was eluted with 0.5 ml of 0.5% formic acid. For each of these treatments, a centrifuge was used.

The eluted peramine was concentrated and then determined by reversed phase liquid chromatography using a Waters Radial-Pak Resolve $C_{18}$ column.

The detection of peramine was performed with a detector employing a fixed wave length of 280 nm.

As a mobile phase, a guanidinium formate solution containing 33% aqueous acetonitrile, pH 3.7 was used.

This buffer was prepared by adding to 1.44 g/l of guanidinium carbonate 1.6 ml/l of 98–100% reagent grade formic acid and 330 ml/l of chromatography grade acetonitrile before degassing with adjustment of volumes with water.

According to the above-described procedures, peramine was detected. As a result, 'Gly-P' exhibited the same strong absorption at 280 nm at a retention time of 6–7 min as that detected in the peramine standard solution. Thus, it was confirmed that 'Gly-P' is producing peramine. However, peramine was not detected in individuals other than 'Gly-P'.

(3) Insect Resistance Test against *Pediasia teterrellus* Zincken

Using 'Gly-P' and peramine non-producing strains, insect resistance test against *Pediasia teterrellus* Zincken was performed. Adults of *Pediasia teterrellus* Zincken flown in for oviposition were captured in a field of Korean lawn grass and allowed them to lay eggs. The eggs were sterilized with 70% ethanol and incubated in an incubator at 25° C. for 7 days for hatching. For the assay, 'Gly-P' and 70 individuals of peramine non-producing strains were used. The assay was performed as follows. On a plastic laboratory dish 9 cm (diameter)×1 cm (height), a wet filter paper was laid. Leaf pieces cut into 1 cm in length were placed on the filter (3 pieces/individual) and the experiment was performed in triplicate. About 200 first-instar larvae of *Pediasia teterrellus* Zincken per dish were left free in the dish. 24 hours thereafter, the presence or absence of damage by larvae (i.e., eaten spots) in leaf pieces was examined.

As a result, no damage was observed in 'Gly-P', but all the leaf samples from the 70 peramine non-producing individuals were eaten up.

(4) Turf Test

An insect damage assay was performed in a field by preparing a 4 $m^2$ turf for Gly-P and each of 5 individuals of peramine non-producing strains. Fertilizers were applied once or twice a month from March to October to give annual amounts applied of 20 kg/10 ares for nitrogen, 20 kg/10 ares for $P_2O_6$ and 20 kg/10 ares for $K_2O$. Trimming was performed 1–3 times in every 3 weeks so that the height of the turf became 50–100 mm. No disease or past control was performed during the growth period of the turf.

As a result, a peak of occurrence of *Pediasia teterrellus* Zincken was observed from late in May to the beginning of June, from late in July to the beginning of August and in mid-September. Due to this, all of the 5 peramine non-producing strains suffered damage by *Pediasia teterrellus* Zincken larvae and the turfs formed with these strains became almost bare. On the other hand, the turf formed with 'Gly-P' was not damaged at all.

(5) Propagation of 'Gly-P'

The propagation of 'Gly-P' was performed by division. 'Gly-P' tillered well when trimmed low. One seedling can be obtained by pulling out a tillered stock from a pot and picking out a tiller by hand. This seedling is planted in a new pot and, by repeating these procedures, propagation can be achieved.

What is claimed is:

1. A new and distinct variety of *Glyceria ischyroneura* Steud., as herein illustrated and described.

* * * * *